(12) United States Patent
Niazi (10) Patent No.: US 9,321,805 B2
(45) Date of Patent: Apr. 26, 2016

(54) DOWNSTREAM BIOPROCESSING DEVICE

(71) Applicant: Therapeutic Proteins International, LLC, Chicago, IL (US)

(72) Inventor: Sarfaraz K. Niazi, Deerfield, IL (US)

(73) Assignee: Therapeutic Proteins International, LLC, Chicago, IL (US)

( * ) Notice: Subject to any disclaimer, the term of this patent is extended or adjusted under 35 U.S.C. 154(b) by 458 days.

(21) Appl. No.: 13/940,793

(22) Filed: Jul. 12, 2013

(65) Prior Publication Data
US 2013/0296538 A1 Nov. 7, 2013

Related U.S. Application Data

(63) Continuation of application No. 13/400,627, filed on Feb. 21, 2012, now Pat. No. 8,506,797.

(51) Int. Cl.
*C07K 1/22* (2006.01)
*B01D 15/02* (2006.01)
(Continued)

(52) U.S. Cl.
CPC . *C07K 1/22* (2013.01); *B01D 15/02* (2013.01); *B01D 15/1892* (2013.01); *B01D 15/22* (2013.01); *B01F 7/245* (2013.01);
(Continued)

(58) Field of Classification Search
CPC ...... B01D 15/08; B01D 15/12; B01D 15/125; B01D 15/14; B01D 15/20; B01D 15/203; B01D 15/22; B01D 15/26; B01D 15/265; B01D 15/38; B01D 15/3804; B01D 15/3809; B01D 17/12; B01D 36/00; B01D 36/02; B01D 37/04; B01D 37/041; B01D 15/02; B01D 15/18; B01D 15/1892; C07K 1/16; C07K 1/22; C07K 1/34; C07K 1/36; C12M 47/04; C12M 47/10; C12M 47/12; C12M 47/20; C12Q 1/06; C12Q 1/68; C12Q 1/6813; C12Q 1/6825; C12Q 1/6834; C12Q 2565/137; C12Q 2565/627; G01N 21/01; G01N 21/0106; G01N 21/0193; G01N 21/018; G01N 21/0125; G01N 21/0162; G01N 21/0168; G01N 30/06; G01N 30/14; G01N 30/16; G01N 30/20; G01N 30/32; G01N 30/72; G01N 30/7233; G01N 30/74; G01N 21/55; G01N 2030/328; G01N 33/53; G01N 33/543; G01N 33/566; G01N 33/577; G01N 30/38; G01N 30/387
See application file for complete search history.

(56) References Cited

U.S. PATENT DOCUMENTS 3,615,222 A * 10/1971 Mead ................... B01L 3/5082
                                                              210/282
3,768,979 A * 10/1973 Mead .................. G01N 33/487
                                                              206/219

(Continued)

OTHER PUBLICATIONS

Yigzaw et al, "Exploitation of the adsorptive properties of depth filters for host cell protein removal during monoclonal antibody purification", published in Biotechnology Progress, 2006, vol. 22, pp. 288-296.*

(Continued)

*Primary Examiner* — Joseph Drodge
(74) *Attorney, Agent, or Firm* — Therapeutic Proteins International, LLC; Cheryl Liljestrand; Sarfaraz Niazi (57) ABSTRACT

Large-scale downstream processing of secreted recombinant proteins is provided in a single device, wherein the contents of a plurality of bioreactors are combined simultaneous to their harvesting and purification resulting in significant savings of time and the cost of manufacturing.

8 Claims, 1 Drawing Sheet

(51) Int. Cl.
  *B01D 15/18* (2006.01)
  *B01D 15/22* (2006.01)
  *C07K 1/34* (2006.01)
  *C12Q 1/06* (2006.01)
  *C12Q 1/68* (2006.01)
  *G01N 30/20* (2006.01)
  *G01N 30/38* (2006.01)
  *C12M 1/02* (2006.01)
  *B01F 7/24* (2006.01)
  *C12M 1/00* (2006.01)

(52) U.S. Cl.
  CPC .. *C07K 1/34* (2013.01); *C12M 1/02* (2013.01); *C12M 47/12* (2013.01); *C12Q 1/06* (2013.01); *C12Q 1/68* (2013.01); *G01N 30/20* (2013.01)

(56) References Cited

U.S. PATENT DOCUMENTS

| | | | | |
|---|---|---|---|---|
| 4,384,957 A * | 5/1983 | Crowder, III | B01D 15/22 | 210/198.2 |
| 4,550,594 A * | 11/1985 | Engstrom | B01D 15/22 | 210/198.2 |
| 4,816,161 A * | 3/1989 | Olness | B01D 61/28 | 210/266 |
| 4,879,030 A * | 11/1989 | Stache | B01D 61/002 | 210/238 |
| 4,976,866 A * | 12/1990 | Grinstead | B01D 15/00 | 210/256 |
| 5,221,483 A * | 6/1993 | Glenn | A61L 2/0017 | 210/321.64 |
| 5,423,982 A * | 6/1995 | Jungbauer | B01D 15/14 | 210/198.2 |
| 5,698,004 A * | 12/1997 | Hartmann | C05C 7/00 | 71/55 |
| 5,843,788 A * | 12/1998 | Rexroad, Jr. | G01N 30/88 | 436/161 |
| 5,855,789 A * | 1/1999 | Smith | B01J 41/043 | 210/670 |
| 6,048,374 A * | 4/2000 | Green | C10B 7/10 | 110/235 |
| 6,168,711 B1 * | 1/2001 | Teramachi | B01D 53/84 | 210/123 |
| 6,265,224 B1 * | 7/2001 | Collis | C12Q 1/6806 | 204/524 |
| 6,610,528 B1 * | 8/2003 | Mathur | C12Q 1/24 | 435/174 |
| 6,740,241 B1 * | 5/2004 | Dickson | B01D 15/08 | 141/12 |
| 6,797,174 B2 * | 9/2004 | Neuroth | G01N 30/6091 | 210/198.2 |
| 6,923,907 B2 * | 8/2005 | Hobbs | B01F 13/0059 | 210/198.2 |
| 6,987,263 B2 * | 1/2006 | Hobbs | G01N 30/6043 | 250/287 |
| 7,143,527 B2 * | 12/2006 | Garcia | H01L 21/67034 | 134/902 |
| 7,226,535 B2 * | 6/2007 | Hubbuch | B01D 15/02 | 210/198.2 |
| 7,270,784 B2 * | 9/2007 | Vuong | G01N 35/1074 | 422/105 |
| 7,306,934 B2 * | 12/2007 | Arora | B01D 61/425 | 435/177 |
| 7,311,880 B2 * | 12/2007 | Perman | B01L 3/50255 | 422/267 |
| 7,608,583 B2 * | 10/2009 | Sahib | C07K 14/62 | 514/1.1 |
| 8,506,797 B2 * | 8/2013 | Niazi | C07K 1/22 | 210/149 |
| 8,668,886 B2 * | 3/2014 | Niazi | C12M 23/14 | 210/178 |
| 8,852,435 B2 * | 10/2014 | Niazi | B01D 15/22 | 210/638 |
| 2001/0043714 A1 * | 11/2001 | Asada | H04R 5/02 | 381/399 |
| 2002/0150926 A1 * | 10/2002 | Jindal | G01N 30/463 | 435/6.12 |
| 2003/0022243 A1 * | 1/2003 | Kondejewski | G01N 33/6896 | 435/7.1 |
| 2003/0091976 A1 * | 5/2003 | Boschetti | C07K 1/16 | 435/4 |
| 2005/0186177 A1 * | 8/2005 | Michael | A61K 38/215 | 424/85.6 |
| 2005/0236312 A1 * | 10/2005 | Gebauer | B01D 15/206 | 210/198.2 |
| 2005/0238641 A1 * | 10/2005 | Burton | A61L 2/0011 | 424/140.1 |
| 2006/0266684 A1 * | 11/2006 | Pichl | B01D 15/14 | 210/198.2 |
| 2007/0219524 A1 * | 9/2007 | Burnouf | A61J 1/10 | 604/408 |
| 2007/0221557 A1 * | 9/2007 | Barber | B01D 15/20 | 210/198.2 |
| 2008/0017569 A1 * | 1/2008 | Ramsey | B01D 67/0004 | 210/490 |
| 2008/0022630 A1 * | 1/2008 | Fuss | B32D 5/0073 | 53/79 |
| 2008/0255027 A1 * | 10/2008 | Moya | C07K 1/30 | 514/1.1 |
| 2009/0014389 A1 * | 1/2009 | Noyes | B01D 15/206 | 210/656 |
| 2009/0188211 A1 * | 7/2009 | Galliher | B01F 13/0827 | 53/434 |
| 2010/0230355 A1 * | 9/2010 | Kerr | B01D 15/1892 | 210/657 |
| 2010/0285593 A1 * | 11/2010 | Amoura | G01N 30/06 | 436/8 |
| 2010/0310548 A1 * | 12/2010 | Yeh | A61K 39/39591 | 424/130.1 |
| 2011/0085983 A1 * | 4/2011 | Le | G01N 30/14 | 424/9.2 |
| 2011/0117538 A1 * | 5/2011 | Niazi | C12M 29/06 | 435/5 |
| 2011/0198286 A1 * | 8/2011 | Niazi | C12M 23/14 | 210/638 |
| 2012/0016113 A1 * | 1/2012 | Niazi | B01J 20/2805 | 530/417 |
| 2013/0017577 A1 * | 1/2013 | Arunakumari | C07K 16/00 | 435/71.1 |
| 2013/0177919 A1 * | 7/2013 | Kaufmann | C07K 14/4702 | 435/6.13 |

OTHER PUBLICATIONS

Shukla et al, "Strategies to address aggregation during protein A Chromatography", published in Bioprocess International, May 2005, pp. 36-44.*

* cited by examiner

DOWNSTREAM BIOPROCESSING DEVICE

CROSS REFERENCE TO RELATED APPLICATION

This application is a continuation of U.S. patent application Ser. No. 13/400,627, entitled "DOWNSTREAM BIOPROCESSING DEVICE" filed on Feb. 21, 2012, the contents of which are incorporated herein by reference in its entirety.

FIELD OF THE INVENTION

The instant invention relates generally to the field of large-scale manufacturing of target proteins using biological cultures that secrete target proteins wherein the contents of a plurality of bioreactors are combined simultaneous to their harvesting and purification in a downstream bioprocessing device resulting in significant savings of time and the cost of manufacturing.

BACKGROUND OF THE INVENTION

Large scale manufacturing of target proteins using mammalian cells such as Chinese Hamster Ovary Cells (CHO) or other similar cells currently constitutes about three-fourth of all recombinant manufacturing methods used today. As more target proteins, particularly the monoclonal antibodies (MABs) come off patent, there is a rising unmet need for manufacturing systems that will be affordable, easily installed and operated with least burden of regulatory challenges. None of the currently used systems, regardless of their cost, offer these advantages. As an example, a mammalian cell manufacturing facility to provide at least 20% of the world market for a single MAB could cost over $100 Million for cGMP production. Needs for such large investment have kept many companies outside of this field of manufacturing resulting in monopolization and price controls for these products worldwide.

There is a large unmet need to develop methods for manufacturing of target protein at the lowest possible cost and these can be achieved by a novel combination of various concepts including:
use of smaller bioreactors to create large batches by combining the output in compliance with CFR21 requirement of the definition of a cGMP batch, to reduce the cost of scaling up and validation, reduced cost of contamination failures and using smaller manufacturing facilities;
eliminating the costly steps of cell separation, nutrient media volume reduction and lengthy chromatography column loading;
allowing purification using either step or gradient elution; and,
performing all of the above operations in a single container under fully automated conditions to allow for unattended operations.

The instant invention provides a novel solution for cost-containment in target protein manufacturing by combining all of the above key elements in a novel system that can be used to manufacture mainly the type of target proteins which are secreted in the nutrient media, more particularly the large dose products like monoclonal antibodies with least capital cost requirement and with the lowest possible operating cost, and the shortest turn-around time for development and manufacturing of new products. More generally, the instant invention can be used to pool, harvest and purify any recombinant substance either as expressed or in any stage of purification. Representative examples will the pooling and concentration of target proteins target proteins at the stage of refolding of proteins.

The novel downstream processing system claimed is not an obvious outcome of the known art; several novel steps, hardware components and methods had to be created to make this system to function optimally.

BRIEF DESCRIPTION OF THE INVENTION

A pharmaceutical production batch size is defined in accordance with the CFR21 (Code of Federal Register) as a homogenous mixture of ingredients. A "batch" or "lot" as defined in the WHO GMP guideline (TRS 908 Annex 4) as "a defined quantity of starting material, packaging material, or product processed in a single process or series of processes so that it is expected to be homogeneous. It may sometimes be necessary to divide a batch into a number of sub-batches, which are later brought together to form a final homogeneous batch. In the case of terminal sterilization, the batch size is determined by the capacity of the autoclave. In continuous manufacture, the batch must correspond to a defined fraction of the production, characterized by its intended homogeneity. The batch size can be defined either as a fixed quantity or as the amount produced in a fixed time interval."

In those instances where smaller sub-batches are manufactured and pooled together, it requires combining them in a larger container wherein the sub-batches can be mixed to a homogenous mixture. However, in many situations, a larger container use can be prohibitive such as in clean rooms and thus there is an unmet need to invent systems that will allow mixing between containers without the need to mix the entire content in a larger container.

The idea of mixing contents of multiple containers also offers many significant financial and regulatory advantages.

There are additional advantages in combining smaller sub-batches to produce a larger batch. The science of pharmaceutical manufacturing teaches us that changing the size of a batch is not a simply exercise. As the size of a batch changes, the dynamics of mixing also changes along with the dynamics of any reactions taking place in the manufacturing process and as a result a manufacturer is required to conduct studies to validate the conditions of manufacturing to assure that a specific size of a batch would consistently result in the same product. Therefore manufacturers are required to invest substantial time and money in validating different batch sizes to meet their need for specific quantities of the product.

Biological manufacturing of products such as proteins using bioreactors even faces greater challenges as changes in the volume of liquid (nutrient media and biological culture) in the bioreactor container significantly changes the conditions required to produce a product consistently. The factors that are of significant importance include the geometry of the container, the amount of gasification, the amount and the nature of agitation of the liquid and as a result it is not possible to predict the behavior of manufacturing process unless it is practiced and appropriate corrections made to various parameters of the manufacturing process.

Since the manufacturers of products are often faced with a choice of making a larger or a smaller batch at a time, the most obvious exercise conducted is to validate several batch sizes and use a specific batch size based on the current need of manufacturing. The use of different batch sizes also require making available different size of vessels, and other technical attachments to a bioreactor, making the cost of maintaining several validated batch sizes very high. However, as target proteins are the most expensive to manufacture and often have a shorter shelf life, it is inevitable for the manufacturers not to maintain several validated batch sizes.

Since bioreactors mainly employ liquid contents, they are easier to mix and finding a solution to mix the contents of several bioreactors in a manner that it would meet the requirement of the FDA in accordance with CFR21 for a single batch would reduce the cost of manufacturing significantly by reducing the number of batches that need to be validated and affording the flexibility to manufacturers to produce different sizes of batches at will using fewer variations in the manufacturing equipment.

There is no prior art that teaches on combining the contents of several bioreactors in a continuous manner using much smaller mixing vessels to constitute a single batch. The instant invention not only resolves this critical hurdle in reducing the cost of production but also teaches a commercial level applications where hundreds and thousands of liters of liquid can be processed using low-cost solution to mix liquids. The instant invention offers a two-step method for uniting very large volumes of nutrient media from several bioreactors; first, all bioreactors pour into a small mixing plenum, which then introduces the liquid into a much smaller container compared to the size of the bioreactor. The intent is not to hold but to continuously mix and drain out the nutrient media and the biological culture and only keep the active target protein by binding it to a resin capable of binding it.

The instant invention provides a continuous mixing capturing of target protein. Traditionally, once a target protein has been expressed in a bioreactor, the process of harvesting and purification currently requires separation of cells, reduction in the volume of nutrient media and loading of chromatography columns. All of these are extremely time consuming steps, cause substantial degradation of the expressed target protein and require very large capital investment.

The instant invention combines all processes, more particularly for target proteins like monoclonal antibodies, by first capturing the expressed target proteins target proteins using a chromatography media capable of binding the target protein and then discarding the nutrient media and the biological culture; the complex of target protein and chromatography media is then washed and finally eluted to obtained highly purified form of target protein using a unitary downstream bioprocessing into which the bioreactors drain.

The present invention capitalizes on the recent availability of many resins that are capable of binding target proteins in large quantities. Most modern resins will bind between 20-125 mg of target protein per mL of resin. Many of these resins are highly specific to the target proteins and many of them can be combined to remove any type and quantity of a target protein from a solution by a simple process of physicochemical binding that is strong enough to retain the target proteins attached to the resin while the nutrient medium is removed from the bioreactor. The art has also advanced significantly in the field of target protein purification wherein we now have a much better ability to elute these bound target proteins from resins by adjusting the pH, the ionic strength or other characteristics of the eluting buffer to break the binding between the resin and the target protein. This allows removal of target proteins from a bioreactor as a highly concentrated solution that is ready for further purification and in some instances it can even be the final product for use.

Affinity chromatography is a separation technique based upon molecular conformation, which frequently utilizes application specific resins. These resins have ligands attached to their surfaces, which are specific for the compounds to be separated. Most frequently, these ligands function in a fashion similar to that of antibody-antigen interactions. This "lock and key" fit between the ligand and its target compound makes it highly specific.

Many membrane products are glycoprotein and can be purified by lectin affinity chromatography. Detergent-solubilized products can be allowed to bind to a chromatography resin that has been modified to have a covalently attached lectin.

Immunoaffinity chromatography resin employs the specific binding of an antibody to the target protein to selectively purify the target protein. The procedure involves immobilizing an antibody to a column material, which then selectively binds the target protein, while everything else flows through.

Some of the state of the art resins binding technologies include:

a. novozymes's newly patented Dual Affinity Polypeptide technology platform replaces Protein A process steps with similar, but disposable, technology;

stimuli responsive polymers enable complexing and manipulation of target proteins and allow for control of polymer and target protein complex solubility, which results in the direct capture of the product without centrifuges or Protein A media, from Millipore Corp.;

mixed mode sorbents to replace traditional Protein A and ion exchange, for improved selectivity and capacity with shorter residence times. These media, with novel chemistries, include hydrophobic charge induction chromatography, such as MEP, and Q and S HyperCel from Pall Corp;

monoliths, involving chromatography medium as a single-piece homogeneous column, such as Convective Interaction Media monolithic columns from BIA Separations;

simulated moving beds, involving multicolumn countercurrent chromatography, such as BioSMB from Tarpon Biosystems;

protein G (multiple vendors);

single domain camel-derived (camelid) antibodies to IgG, such as CaptureSelect from BAC; new inorganic ligands, including synthetic dyes, such as Mabsorbent A1P and A2P from Prometic Biosciences;

expanded bed adsorption chromatography systems, such as the Rhobust platform from Upfront Chromatography;

ultra-durable zirconia oxide-bound affinity ligand chromatography media from ZirChrom Separations;

Fc-receptor mimetic ligand from Tecnoge;

ADSEPT (ADvanced SEParation Technology) from Nysa Membrane Technologies;

membrane affinity purification system from PurePharm Technologies; custom-designed peptidic ligands for affinity chromatography from Prometic Biosciences, Dyax, and others;

protein A- and G-coated magnetic beads, such as from Invitrogen/Dynal;

new affinity purification methods based on expression of target proteins or MAbs as fusion target proteins with removable portion (tag) having affinity for chromatography media, such as histidine) tags licensed by Roche (Genentech);

protein A alternatives in development, including reverse micelles (liposomes), liquid-nutrient medium extraction systems, crystallization, immobilized metal affinity chromatography, and novel membrane chromatography systems; and, plug-and-play solutions with disposable components (e.g., ReadyToProcess), process development ÄKTA with design of experiments capability, and multicolumn continuous capture, from GE Healthcare.

It is surprising that while great advances have been made in the design of resins available to capture target proteins, these have been only used in the downstream processing of purification. Adding resins to a crude mixture of target proteins and host cells will be no different than the current practice of art that teaches first concentrating the nutrient media and then loading it onto columns with all of the impurities in it.

Aiming at a cell line that produces 1 mg/mL of target protein and that the binding capacity of the resin used is 50 mg/mL, this will require 20 L of resin when operating a 1000 L bioreactor. The cost of resins suitable for the manufacturing of monoclonal antibodies can range from $15-$20,000 per liter, such as Protein A. As a result, most manufacturers would rather run several sub-batches of purification using a smaller quantity of the resin. However, given that these can be used for hundreds of times, the cost is readily amortized for use and avoids the tediousness and regulatory hurdles in preparing sub-batches.

The biological components that may be processed in accordance with the invention are described in the paragraphs which follow and include, but are not limited to, cell cultures derived from sources such as animals (e.g., hamsters, mice, pigs, rabbits, dogs, fish, shrimp, nematodes, and humans), insects (e.g., moths and butterflies), plants (e.g., algae, corn, tomato, rice, wheat, barley, alfalfa, sugarcane, soybean, potato, lettuce, lupine, tobacco, rapeseed (canola), sunflower, turnip, beet cane molasses, seeds, safflower, and peanuts) and human. The only requirement is that the biological culture used should express the target protein by secreting it in the nutrient media as opposed to the formation of inclusion bodies in some instances.

DETAILED DESCRIPTION OF THE INVENTION

The instant invention provides a means of connecting a plurality of pre-validated, smaller-scale bioreactors to a downstream bioprocessing device holding a chromatography media capable of binding the target protein in the nutrient media of the bioreactors ready for harvesting.

The nutrient media and the biological culture are allowed to enter the downstream bioprocessing device causing the chromatography media to float upwards and thus creating and expanded bed chromatography system. A significant modification to the classical expanded bed chromatography is provided in the instant invention wherein the chromatography resin is kept in a continuous state of uniform distribution throughout the container, a cylinder, that holds the nutrient media, the biological culture and the chromatography media. This modification is crucial to the success of the downstream bioprocessing device and also to provide it to operate unattended and automatically.

As the nutrient media and the biological culture rise to the top of the downstream bioprocessing device, these flow out while the chromatography media is held in the downstream bioprocessing device as a filter is installed in the downstream bioprocessing device; the porosity of the filter is smaller than the size of chromatography resin (generally 50-300 microns). By calculating the quantity of chromatography media such as Protein A resin accurately through prior experimentation of the binding capacity of the target protein, one can assure that the entire quantity of target protein is bound to chromatography media.

However, it is well-realized that a certain reaction time is required for the binding to take place, so the flow rate of nutrient media from the bioreactors into the downstream bioprocessing device must be carefully controlled; one test for the correctness of the flow rate is the measure of recombinant product concentration in the nutrient media that reaches the top of the downstream bioprocessing device and is decanted. A continuous monitoring of the concentration of target protein will allow adjusting the flow rates. Generally, the out-flowing nutrient media should not contain more than 1% of the incoming concentration of the target protein; sampling the incoming nutrient media and using it as a reference while the nutrient media exiting the device is treated as a test item determine this. Only when the ratio of the concentration between in the incoming and outgoing media is 1:100 that the nutrient media is allowed to flow through; generally a cut off range will be 1:100 to 2:100 to conserve the maximum quantity of target protein and provide the highest efficiency of the device.

Once the entire nutrient media and the biological culture is removed from a plurality of the bioreactors and passed through the downstream bioprocessing device, the bioreactors are sealed at the bottom outlet. The target proteins-media complex in the downstream bioprocessing device is washed by adding a washing buffer through an inlet at the bottom of the device and allowed to flow out from the top port until a pre-determined level of debris is removed. It is then followed by introducing an elution buffer to break the bonding between the media and the target proteins, either by passing the elution buffer through the bottom port and collecting pure target protein solution through the upper port or by allowing the chromatography media to settle down in the downstream bioprocessing device and allowing the elution buffer to pass through the compacted bed of the chromatography media and collecting the pure solution of target protein through the bottom port.

The above invention is operated in a manner where only gravity flow is used to transfer the nutrient media from the bioreactors to the downstream bioprocessing device by placing the inlet port of the downstream bioprocessing device below the level of the outlet port of the bioreactors. Placing the bioreactors around the downstream bioprocessing device and using the same length of connecter tubes can uniformly maintain the flow rates across many bioreactors. Obviously, there are many mechanical means of transporting the nutrient media to the downstream bioprocessing device and these include use of various pumps that may equally be useful. However, the use of gravity assures that the degradation of target protein is minimized during the transfer process.

Figure 1:
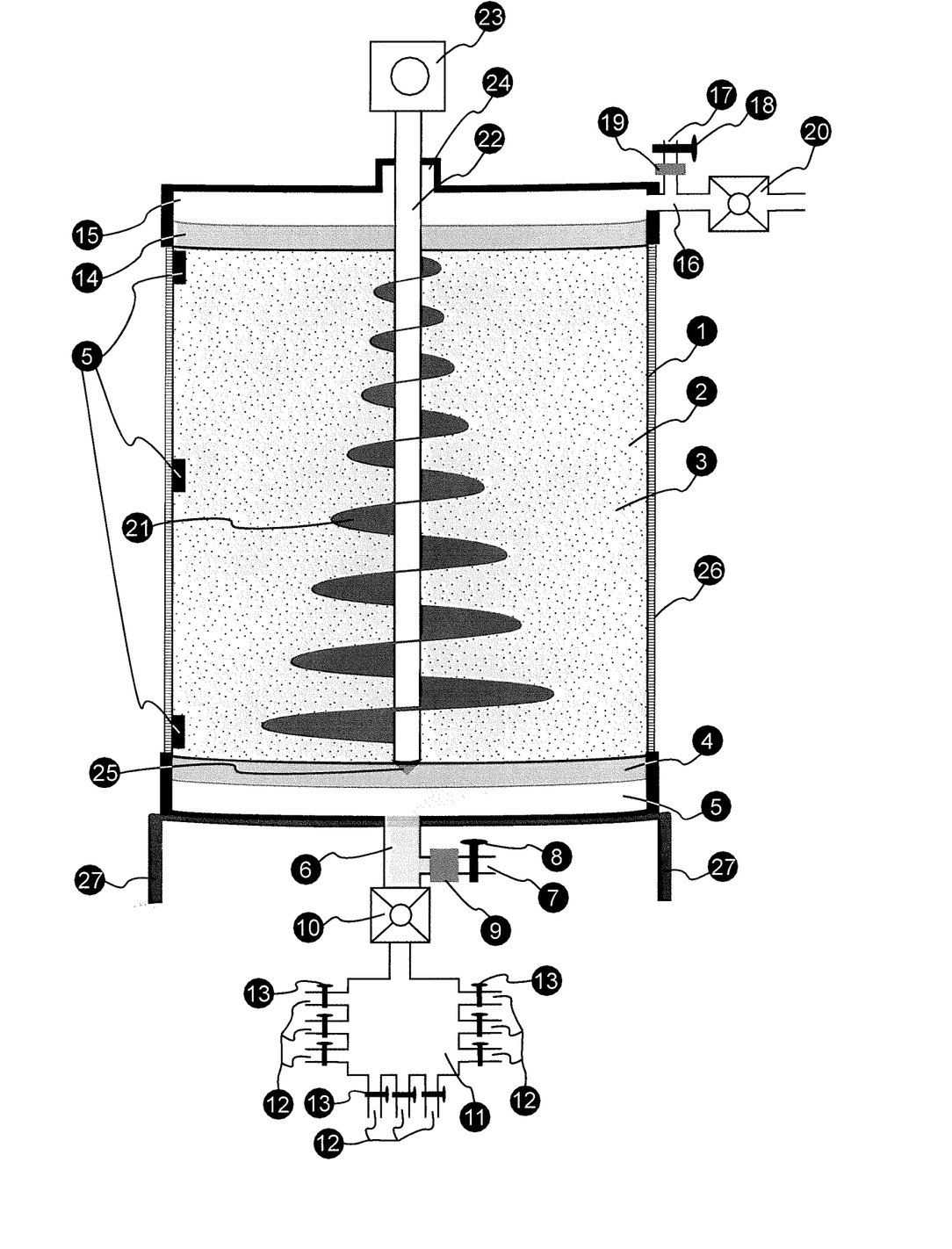
FIG. 1 shows a cross-sectional side view of the claimed downstream processing device.

The claimed device has many unique and specific features that are required for its optimal operation. It comprises a cylinder 1, a cylindrical, hard-walled container that serves as the main processing space for the nutrient media and biological culture 2 entering the cylinder 1 from a plurality of bioreactors. The volume of the cylinder 1 is important in some instances for one reason and is important for another reason in another instance. When operating it to perform as an expanded-bed chromatography system to capture and to purify the target protein, the height of the cylinder 1 is important to allow it enough dwell time as nutrient media flows upwards through a column chromatography resin 3. The volume of cylinder 1 is optimally at least 1.5-3 times the volume of chromatography resin 3 in the cylinder 1. Generally, an optimal relationship of the diameter of the cylinder 1 and its height would also be established from simple studies of the efficiency of binding of a target protein to a chromatography resin; these are specific binding reactions and whereas the capacity of binding of the resin may be known, the rate of binding will depend on many factors including the time allowed for contact, temperature of nutrient media and the agitation of the nutrient media. It should be realized that the claimed device provides an expanded chromatography column to bind the target protein to the chromatography resin; the longer is the time allowed to bind, the higher will be the binding; however, physical limitations of the height of the column and other considerations as discussed below pertaining to purification of the target proteins will limit on the height of the cylinder 1 used.

The chromatography resin 3 is retained in the cylinder 1 by providing a bottom filter 4 that has a porosity smaller than the diameter of the chromatography resin 3; this would generally be 50-300 microns; note that in typical chromatography preparative column a much finer filter is used requiring often application of pressure or requiring very long times for a buffer to pass through a bed of chromatography resin. The bottom filter 4 is kept in place by a bottom cap 5 that can be removed for a complete cGMP cleaning of the device and also to remove the chromatography media 3, which is reused. The bottom cap 5 has a bottom liquid port 6, which would generally be in the center of the cap; the bottom liquid port 6 has a bottom sampling port 7, which in turn has a bottom sampling port control valve 8 to start and stop flow of nutrient media and a filter 9 to remove biological culture prior to sampling. The bottom liquid port 6 has a bottom flow control valve 10, and connected to a plenum 11 with a plurality of ports 12 and control valves 13 attached to each of the plenum ports 11; the plenum 11 is capable of being connected to other bioreactors and sources of a washing or elution buffer and also be used to allow a washing buffer or elution buffer to exit the device.

The top side of the cylinder 1 is also supplied with a top filter 14 to retain the chromatography resin 3; the top filter 14 is kept in place by a top cap 15 that has at least one upper liquid port 16 to which is connected an upper sampling port 17 and a upper sampling port valve 18 to start and stop sampling of the nutrient media and a filter 19 to remove biological culture prior to sampling. The upper liquid port 16 is connected to an upper flow control valve 20, which then discharges the nutrient media out and is also used to introduce an eluting buffer in a packed column mode purification protocol.

Inside the cylinder 1 is installed an auger 21 connected through an auger shaft 22 to a motor 23 placed outside of the cylinder 1; the shaft 22 passes through a sealed ball-bearing 24 installed in the center of the top filter 14 and through a hole in the center of the top cap 15; the bottom of the auger shaft 22 rests in an auger shaft socket 25 that is embedded in the bottom filter 4; this helps prevent wobbling of the auger when it is rotated.

The auger 18 is a critical element of the claimed invention; it is conical in shape wherein the larger blades are in the bottom and smaller blades in the top. Since the goal of using the auger is to provide a laminar movement of liquid upwards, the ratio of the diameter of the blade at the bottom and at the top is critical. Optimally, the bottom blade would cover approximately 80% of the diameter of the cylinder 1 and the top blade would approximately be 20% of the diameter of the cylinder 1. When rotated at slow speeds ranging from 1-20 rpm, it creates a gentle movement of the nutrient media from the bottom to the top in a sweeping motion that keeps the flow of the nutrient media laminar. This creates a novel fluid bed of chromatography resin by keeping it uniformly suspended throughout the cylinder. Without this feature, the contact efficiency between the resin and the target proteins target proteins is minimized and the efficiency of capturing the target protein reduced. This becomes more important as the chromatography resin becomes saturated with the target protein. This element of innovation provides a method of completely saturating the chromatography resin while a fast flow of nutrient media is maintained.

It is important to maintain a Reynolds number (Re) of less than 10,000 in the cylinder; this number is determined by five factors: the density, the viscosity, the diameter of the agitator, the rotational speed of the agitator (rpm) by the following equation in a stirred vessel: $Re=[(\rho ND^2)/\mu]$, where $\rho$ the density is and $\mu$ is the viscosity; ND is velocity as D is the diameter and N is the rotational speed (RPM) [R. K. Sinnott Coulson & Richardson's Chemical Engineering, Volume 6: Chemical Engineering Design, 4th Ed (Butterworth-Heinemann) page 473].

The cylinder 1 has additional means of heating or cooling 26 to keep the nutrient media at an optimal temperature; it is noteworthy that the claimed device provide a continuous flow of the nutrient media but the flow rate is at a slower speed and so it is possible to maintain a certain temperature given the standard coefficients of heat exchange with the wall of the cylinder 1. A variety of methods are described and include using a jacketed cylinder 1, wrapping the cylinder 1 with a heating or cooling blanket, exposing the cylinder to an infrared lamp when the goal is heat the contents and many other devices widely available in the art.

The claimed device is vertically placed on a support 27 that is generally a ring stand but any other means suitable to firmly place the claimed device in a vertical position would work. It is noteworthy that the claimed invention utilized a gravitational flow method of transferring nutrient media from the bioreactors to the claimed device; for this reason, the means of supporting 26 should be of such mechanical nature that it will allow the claimed invention to rest at a level lower than the lowest part of the bioreactor from which the nutrient media is removed and transferred to the claimed invention.

The target protein-harvesting and purification device described in the FIGURE above is generally used at the end of the bioreactor cycle wherein a plurality of bioreactors is simultaneously connected to the claimed device. The amount of chromatography media contained in each device would be easily calculated by the binding efficiency of the target protein For example, Protein A chromatography media shows a binding of 30-50 mg/mL of the chromatography media. Assuming a 1,000 L nutrient media is used in a 2,000 L bioreactor and the production cycle has come to an end, a point where the CHO are no longer producing sufficient quantity of target protein Further assuming that the productivity of the recombinant cell line is about 1 G/L; thus, in this case, there is about 1000 G of target protein in solution in the nutrient media that is to be removed and purified.

On a theoretical basis, assuming a lower end of binding of 30 mg/mL, it will take about 33 L of chromatography media to bind substantially all of target protein in the solution. It should be noted that while Protein A is rather specific to monoclonal antibodies, it is likely that the binding capacity of the chromatographic media will be compromised because of binding of other components in the nutrient media. This can be readily studied by withdrawing a small volume of the nutrient media and adding to it incremental amounts of the chromatography media used until the concentration of the target protein in solution reaches to a pre-determined low value. This would be called titrating the nutrient media.

The instant invention combines the processing of a plurality of bioreactors, for example, as described above, each requiring a 33 L volume of Protein A to purify the target protein. Assuming that the contents of five bioreactors are combined, it will require 165 L of chromatography resin and given that there should be at least twice the volume of the main holding container, it will take a 230 L to process 5000 L of nutrient media; a traditional system of combining 5000 L media would be to combine the individual volumes in a 5000 L container, which is an expensive exercise. Instead, a container less than 10% of the size is all that is required in the instant invention.

Using the instant invention in the example above, nutrient media from several bioreactors will be allowed to enter the main container of the claimed device where the target protein would bind to the chromatography resin as the nutrient media rises from the bottom through a filter disk that retains the chromatography media from leaving the container; another filter at the top retains the media at the top end. The key to a successful capture step is allowing flow nutrient media at a rate that allows optimal binding. Gentle mixing is critical to this invention and this provided by a novel design of an auger blade that pushes the nutrient media upwards.

An optimal process would remove substantially all of target protein from nutrient media; to assure this, the instant invention introduces an automated system of controlling the flow control valves installed at both end of the device; a dual sampling method where the incoming nutrient media and the outgoing nutrient media are continuously sampled and using the incoming nutrient media as the standard, it is easy to calculate the quantity of target protein in the nutrient media flowing out of the device and discarded. Should there be a rise in the concentration of target protein in the drained liquid, the valves close down and retain the nutrient media in the main container until complete binding is reached. Given the large quantity of nutrient media flowing out, an automated system described in the instant invention allows automated operations, a key requirement to large-scale commercial manufacturing.

The instant invention introduces a system of automatically processing the batch wherein the concentration of target protein is measured continuously in two points, the point of entry and the point of exit for the nutrient media; the samples are first filtered through a filter that retains any biological culture to reduce interference from suspended particles. The nutrient media from the entry point is used as a reference sample and the nutrient media from the exist point serves as a sample in a spectrophotometric detection device. The technique of detection is widely available in the prior art and is not claimed. (M. H. Simonian, Spectrophotometric determination of protein concentration, Curr. Protocol. Cell Biol, Appendix 3b, 2002). Absorbance measured at 280 nm A(280) and 205 nm A(205) is used to calculate protein concentration by comparison with a reference but in the instant invention the purpose is not to measure the concentration but a relative concentration between the reference and the standard. Given that there are going to be dissolved impurities and lysates and impure protein in the media, the A(280) and A(205) methods can be used. A spectrofluorometer or a filter fluorometer can be used to measure the intrinsic fluorescence emission of a sample solution; this value is compared with the emissions from reference solutions to determine the relative concentration. There are two colorimetric methods: the Bradford colorimetric method, based upon binding of the dye Coomassie brilliant blue to the protein of interest, and the Lowry method, which measures colorimetric reaction of tyrosyl residues in the protein sample. However, the instant invention does not limit the type of detection method used; with evolving science of detection of proteins, it may be possible to device a battery of tests including spectrophotometric, fluorometric, infrared or lasers to provide a relative measure of the concentration of the target protein in the nutrient media.

Once the entire nutrient media has passed through the container, a washing buffer is used to replace the nutrient media to wash off the chromatography resin on a continuous basis, following which an elution buffer is introduced in a similar manner to collect purified target protein solution in the outflow through the top liquid port. However, several other methods of purification are available for use within the same device design. One of them requires allowing the elution buffer to stay in the container for a length of time to allow complete breakdown of the binding between the chromatography media and the target protein and then removing the elution buffer through the bottom liquid port. Alternately, the washing buffer can be drained out of the bottom liquid port and the chromatography resin allowed to settle down as a packed column when the elution buffer can be introduced through the top liquid port and the elution buffer either as a single buffer or in a gradient elution buffer allowed to pass through the chromatography resin bed to collect various fractions of the elution buffer and the fractions containing the highest concentration and least impurities are combined to provide the final processed product.

In a first embodiment, the instant invention provides a method of combining several sub-batches to produce a large single batch in compliance with the US FDA CFR21 definitions reducing the cost of production by allowing use of smaller bioreactors, reducing the risk of a larger batch going bad and eliminating the capital cost of bioreactors of several sizes and also of a larger container to mix the contents of several bioreactors. This novel approach makes it possible for even small size companies to develop and manufacture large commercial scale batches at the lowest capital and running cost.

The instant invention obviates the need for installing larger bioreactors when larger quantities of target proteins are produced. The regulatory compliance of mixing smaller sub-batches to make a larger batch is met by allowing the contents of a plurality of bioreactors to mix in a plenum prior to entering the claimed device; secondly, as the entire contents of a plurality of bioreactors is passed through the claimed device containing a fixed quantity of a chromatography resin, the captured target proteins target proteins constitutes a single batch in a smaller quantity of volume and thus reducing the problems related to handling large containers;

In a second embodiment, the present invention provides a method of avoiding several steps in the harvesting of target proteins including separation of cells, reducing the volume of nutrient media and loading of chromatography column, all of which add substantially to capital cost of equipment, cost of running the equipment, lengthy times required to complete these steps and causing degradation of target proteins. In the present invention, a nutrient media containing host cells and target protein are subjected to a non-specific or specific treatment with chromatography media or a combination of chromatography media contained in the device that would bind all or substantially all of charged or uncharged molecular species, this step is followed by removing the debris of cells and other components from chromatography media-target protein complex by simply washing it with a washing buffer. The present invention thus obviates a major hurdle in the harvesting of products that involves filtering out host cells using a fine filter, not larger than 5μ, to retain host cells such as Chinese Hamster Ovary Cells. When large volume of media is used, this process takes a very long time, adds substantial cost of filters, pumps, containers and space management. This step is then generally followed by a concentrating step wherein the volume of nutrient media is reduced most to one-tenth its volume using a cross-flow or micro filtration process, which takes a very long time to complete and again adds substantial cost of equipment and manpower and in some instances causes degradation of target protein.

The instant invention combines these two steps into one simple step. The argument that if it is the intent to harvest and concentrate target protein from a complex mixture containing host cells, why would it not be more efficient to remove the target protein from the mixture instead of removing other components that are present in much larger quantities. This is what would be considered a contrarian teaching. In the instant invention, those peculiar characteristics of target proteins are exploited to separate them from the rest of the mixture by a non-specific binding to a chromatography media or a mixture of chromatography medias. Obviously, such non-specific capture of target proteins would also capture other components of the mixture and that only requires using a much larger quantity of chromatography media or a specific type of chromatography media that might have specific affinity for the target protein.

The removal of target protein-chromatography media complex is a much simpler process than the removal of host cells or reduction in the volume of mixture; any mechanical process such as decanting, centrifugation or even filtration would work. It is noteworthy that the slowest of all processes would be filtration but even the much larger pore size filter can be used and since the purpose is to collect the filtrate, not the eluate, the cost of manufacturing is lowered substantially.

In a third embodiment, the instant invention allows for the use of a expanded-bed chromatography system to purify a target protein in the same container wherein the target protein is captured. An expanded-bed chromatography system allows for continuous operation of the claimed device and provide automated controls to achieve the highest level of capture and purification in an unattended operation.

The instant invention can also use a mixed-bed chromatography media that may contain an ionic chromatography media, a hydrophobic chromatography media and an affinity chromatography media all used together to optimize the efficiency of harvesting. It is well established that the use of ionic chromatography media does not allow complete capture of products because of the logarithmic nature of ionization; a combination of chromatography medias used in the instant invention allows for a more complete recovery of target proteins.

In a fourth embodiment, the present invention allows purification of a target protein using standard column purification and a gradient elution profile as well as step elution profile; in this comparison, the claimed invention acts similar to a conventional chromatography column with all of its limitations yet without the lengthy steps of loading the column.

In a fifth embodiment, the present invention teaches methods of gravity flow to transfer the contents of a bioreactor to the claimed device; this reduces considerable strain on the target protein is peristaltic pumps are used as it is customary and thus increases the yield of production.

In an sixth embodiment, the present invention teaches the use of a novel mixing component in the device comprising preferably a conical auger that pushes the liquid contents up while maintaining a laminar flow of the liquids reducing strain on the target proteins target proteins and also helping maintain the integrity of the chromatography media; no prior disclosure the use of a mixing system for a chromatography system.

The embodiments described above do not in any way comprise all embodiments that are possible using the instant invention and one with ordinary skills in the art would find many more applications specific to a complex process or even in those processes where such needs might not be immediately apparent.

Prior art on using chromatography media to harvest target protein is non-existent; the U.S. Pat. No. 7,306,934 issued on 11 Dec. 2007 to Arora et al., teaches the use of porous solid ion exchange wafer for immobilizing biomolecules, said wafer comprising a combination of an biomolecule capture-chromatography media containing a transition metal cation of +2 valence; it also teaches a separative bioreactor, comprising an anode and a cathode, a plurality of reaction chambers at least some being formed from a porous solid ion exchange wafers (above) having a combination of art biomolecule capture-chromatography media and an ion-exchange chromatography media and having a genetically engineered tagged biomolecule immobilized on said biomolecule capture chromatography media, each of said porous solid ion exchange wafers being interleaved between a cation exchange membrane and an anion exchange membrane, and mechanism for supplying an electric potential between the anode and the cathode. The instant invention is significantly different from the separative bioreactor taught by Arora. First, the instant invention does not require use of electrodes, chromatography medias with a transition cation of +2 valence or immobilized metal ion affinity chromatography. The use of EDI (electrodeionization) and specific use of tags and limited nature of solvents to remove the captured products mainly enzymes makes this patent teachings distinctly different from the instant invention. Moreover, the Arora patent adds a hardware that adds to the cost of processing purification of products while the instant invention combines several processes into one without adding any new cost element.

The idea of using expanded bed chromatography to purify target protein is know in the prior art such as the U.S. Pat. No. 7,608,583 that teaches purification of insulin using an expanded bed chromatography. The novel aspect of the instant invention is to combine the expanded bed chromatography principles to a process that combines the contents of a plurality of bioreactors, captures and purifies the target protein. However, providing the multi-functionality to a traditional chromatography requires several innovative modifications including a method retaining the chromatography resin in the column at both ends, a means of mixing the contents in the chromatography column and a set of ports and controls that allow use of both step and gradient elution.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for pooling, harvesting and purifying a target protein expressed by a biological culture in a nutrient media in a plurality of bioreactors comprising:
   a. Providing a downstream processing device comprising a cylinder capable of holding a liquid wherein the cylinder comprises:
      i. a top opening comprising a filter covering the top opening and a removable top cap to hold the top filter in place comprising at least one top liquid port and a top flow control valve;
      ii. a top sampling port comprising a top sampling port valve and a top sampling port filter capable of removing a biological culture wherein said top sampling port is connected to one of the top liquid ports of (iii);
      iii. a bottom opening comprising a filter covering the bottom opening and a removable bottom cap to hold the bottom filter disk in place comprising a bottom liquid port, a bottom flow control valve, and a plenum having a plurality of liquid ports wherein said ports are capable of closing and opening;
      iv. a bottom sampling port comprising a bottom sampling port valve and a bottom sampling port filter capable of removing a biological culture wherein said bottom sampling port is connected to the bottom liquid port of (e);
      v. a means of mixing the contents of the cylinder; and
      vi. sensors located at one or more places on or in the cylinder capable of detecting turbidity of the contents of the cylinder;
   b. setting the downstream processing device at such height that the top liquid port is below the lowest level of one or more bioreactors;
   c. connecting the liquid ports of the plenum of (iv) above to one or more bioreactors containing a nutrient media comprising a biological culture capable of producing a target protein;
   d. removing the top cap and adding to the cylinder a quantity of a chromatography media sufficient to bind substantially all of the target protein present in the nutrient media;
   e. replacing the top cap and opening the top and bottom flow control valves;
   f. filling the cylinder with the nutrient media under gravity pressure from the one or more bioreactors;
   g. closing the bottom flow control valve;
   h. mixing the chromatography media to achieve a uniform distribution in the cylinder as indicated by the measurement of turbidity by the sensors of (vi) above and adjusting the speed of mixing to achieve a uniform turbidity;
   i. connecting each of the top and bottom sampling ports to a flow cell of a spectrophotometer capable of measuring the concentration of the target protein and turning on the bottom flow control valve when the ratio of the concentration between the top and bottom sampling ports reaches about 1:100 and closing the bottom flow control valve when the ratio reaches about 2:100;
   j. maintaining the flow of nutrient media from the one or more bioreactors into the cylinder and allowing the nutrient media to flow out of the top liquid port until the contents of the bioreactors have passed through the cylinder;
   k. closing the bottom flow control valve and the liquid ports of the plenum and disconnecting the bioreactors from the plenum;
   l. opening the bottom flow control valve to allow the nutrient media in the cylinder to drain out through one of the unoccupied ports in the plenum and then closing that port;
   m. connecting one or more liquid ports of the plenum to at least one source of washing buffer suitable for removing debris in the cylinder;
   n. starting the flow of the washing buffer into the cylinder through the plenum and allowing the washing buffer to drain out of the top liquid port until a desired level of debris is reached in the drained wash buffer;
   o. stopping the flow of the washing buffer;
   p. opening one of the unoccupied liquid ports in the plenum to allow the washing buffer to drain out of the cylinder and closing that liquid port of the plenum;
   q. connecting one or more liquid ports of the plenum to at least one source of elution buffer capable of breaking the binding of the target protein to the chromatography media;
   r. filling the cylinder with elution buffer and then stopping the flow of elution buffer into the plenum;
   s. closing the bottom flow control valve and begin mixing;
   t. continue mixing the contents of the cylinder for a desired time to allow complete breaking of the binding between the target protein and the chromatography media;
   u. stopping the mixing;
   v. opening the bottom flow control valve and one of the unoccupied liquid ports in the plenum and collecting the elution buffer in a container as a purified concentrated solution of the target protein.

2. The method according to claim 1, wherein steps (n) to (p) are repeated when using more than one washing buffer successively.

3. The method according to claim 1, wherein steps (r) to (v) are repeated when using more than eluting buffer successively in a step elution method.

4. The method according to claim 1, wherein steps (q) to (v) are replaced by following steps:
   a. opening the bottom flow control valve;
   b. adding the elution buffer through the top liquid port at a pre-determined rate;
   c. allowing the eluting buffer to pass through the chromatography media in the cylinder under gravity flow;
   d. collecting the elution buffer as a plurality of timed fractions as it appears through the plenum liquid port; and
   e. pooling the fractions containing the highest concentration of the target protein.

5. The method according to claim 4, where the elution buffer is introduced as a gradient elution buffer.

6. The method according to claim 1, wherein steps (q) to (v) are replaced by the following steps:
   a. opening the top and bottom control valves;
   b. starting the flow of an elution buffer through the plenum into the cylinder;
   c. starting mixing;
   d. allowing the eluting buffer to fill the cylinder and pass through the top filter and collecting a purified form of target protein in the outflow of the eluting buffer through the top liquid port; and,
   e. continuing the flow of the eluting buffer and collection of a purified form of protein until the concentration in the collected eluting buffer reaches a desired level.

7. The method according to claim 1, wherein an automated system controls (1) the opening and closing of ports and valves; (2) mixing; and/or (3) sensor measurements.

8. The method according to claim 1, wherein the cylinder is heated or cooled to maintain a specific temperature.

* * * * *